KENTUCKY BLUEGRASS

Filed Feb. 19, 1974

United States Patent

Plant Pat. 3,782

Patented Sept. 16, 1975

3,782

KENTUCKY BLUEGRASS

Cyril Reed Funk, Jr., East Brunswick, N.J., assignor to Rutgers University, New Brunswick, N.J.

Filed Feb. 19, 1974, Ser. No. 443,377

Int. Cl. A01h 5/00

U.S. Cl. Plt.—88 1 Claim

ABSTRACT OF THE DISCLOSURE

A variety of Kentucky bluegrass having a high level of disease resistance. The variety provides a desirable dark green color throughout the growing season and a good thick dense turf that persists during prolonged periods of high temperatures.

SUMMARY OF THE VARIETY

The present invention relates to a new and distinct variety of *Poa pratensis* which has been designated P–72 Kentucky bluegrass. P–72 is an $F_1$ hybrid between a selection from Bellevue Country Club in Syracuse, N.Y. as female parent and Anheuser Dwarf as male parent. The cross was made during the spring of the year. Seedling progeny from this cross were transplanted to a nursery in August of the same year. The original hybrid was selected in June of the following year. Seed from this plant was used to establish turf plots in New Jersey in September of that year and plots in Marysville, Ohio in September, three years later. Data was obtained from these original plots along with additional seedings that were made at both of the locations and Accokeek, Md. plus nursery and seed yield data at Salem, Oreg.

P–72 Kentucky bluegrass reproduces asexually both apomictically and vegetatively, i.e., by tillers and rhizomes. All asexually reproduced P–72 offspring appear to show complete conformity with the mother plant.

P–72 has a number of highly desirable characteristics including a good level of resistance to *Fusarium roseum, Ustilago striiformis* and *Helminthosporium* spp. type diseases, a desirable dark green color throughout the growing season with good early spring greenup and provides a good thick dense turf that will persist during prolonged periods of high temperatures. These characteristics explain why P–72 will provide good performance in the transition grass growing regions. This transition region is described as the area in which there is a gradual change from growing one adapted species to another or in an area where both cool and warm season grasses will survive but not necessarily provide optimum performance throughout the year.

DETAILED DESCRIPTION OF THE VARIETY

Figure 1:
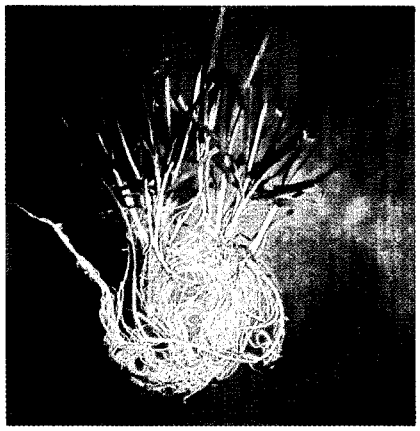
FIG. 1 is a photograph of a P–72 Kentucky bluegrass plant in the vegetative stage including the extensive root and rhizome system.
Figure 2:
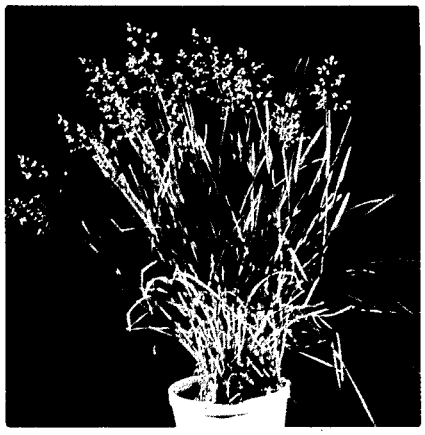
FIG. 2 shows a P–72 Kentucky bluegrass plant in the mature flowering stage. The plant was grown in the field and allowed to flower in the greenhouse.
Figure 3:
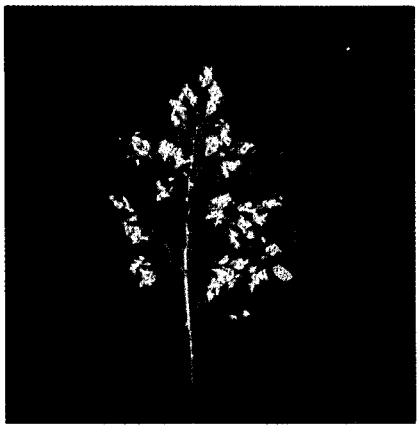
FIG. 3 is a close-up of a flowering panicle of P–72 Kentucky bluegrass grown in the greenhouse.
Figure 4:
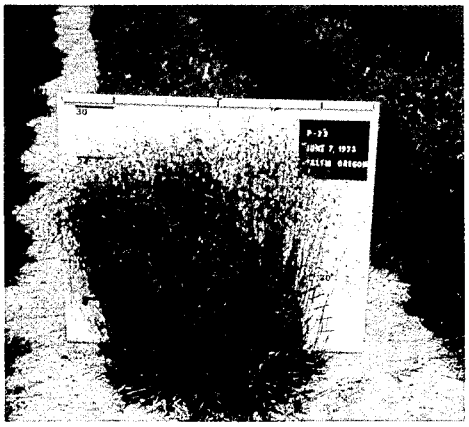
FIG. 4 is a P–72 Kentucky bluegrass plant in flowering stage grown in a seed nursery.

The morphological characteristics of P–72 and other commercially available bluegrass varieties are compared in Table 1. As shown by Table 1, the morphological characteristics of P–72 afford a basis for distinguishing it from other bluegrass varieties.

TABLE 1

Morphological comparison of P–72 and other bluegrass varieties

| Variety | Panicle length in cm. | No. of panicle branch whorls | No. of branches per whorl | | No. of spikelets per whorl | | Length of end spikelet on branch in mm. | | No. of florets per spikelet | Floret length in mm. |
|---|---|---|---|---|---|---|---|---|---|---|
| | | | Lowest | 3d | Lowest | 3d | Lowest | 3d | | |
| P–72 (Marysville, O.) | 9.74 | 5.40 | 4.00 | 2.40 | 35.70 | 19.50 | 5.79 | 5.61 | 5.14 | 2.88 |
| s [1] | .59 | .52 | 0 | .52 | 4.55 | 2.12 | .63 | .46 | .54 | .16 |
| P–72 (Salem, Ore.) | 11.26 | 5.80 | 3.90 | 3.10 | 52.40 | 33.40 | 5.03 | 4.98 | 3.90 | 3.06 |
| s | 1.57 | .42 | .99 | .57 | 19.50 | 7.01 | .41 | 1.13 | .51 | .19 |
| Victa (Marysville, O.) | 7.37 | 4.80 | 5.10 | 3.70 | 35.50 | 20.80 | 5.24 | 5.13 | 4.38 | 3.02 |
| s | .82 | .63 | .32 | .82 | 5.46 | 3.55 | .44 | .45 | .46 | .04 |
| Victa (Salem, Ore.) | 8.98 | 6.30 | 4.90 | 4.30 | 37.80 | 27.00 | 4.31 | 4.35 | 2.96 | 3.11 |
| s | .82 | .67 | .57 | .82 | 8.70 | 6.11 | .32 | .34 | .07 | .14 |
| Merion (Marysville, O.) | 7.20 | 5.00 | 3.50 | 2.10 | 30.90 | 17.50 | 4.27 | 4.06 | 4.51 | 2.44 |
| s | 2.78 | .67 | .53 | .32 | 8.33 | 4.77 | .37 | .26 | .63 | .22 |
| Newport (Marysville, O.) | 8.04 | 4.50 | 4.10 | 2.70 | 32.50 | 15.40 | 4.60 | 4.83 | 3.61 | 3.05 |
| s | 1.12 | .53 | .74 | .95 | 6.28 | 3.31 | .44 | .36 | .46 | .11 |

| Variety | Ligule length in mm. | Leaf [2] blade width in mm. | Plant height in cm. | No. of nodes per plant stem | Length of top internode in cm. | Glume length in mm. | |
|---|---|---|---|---|---|---|---|
| | | | | | | 1st | 2d |
| P–72 (Marysville, O.) | 1.32 | 4.57 | 52.88 | 4.10 | 9.03 | 2.90 | 3.26 |
| s | .15 | .74 | 3.90 | .32 | 2.53 | .21 | .15 |
| P–72 (Salem, Ore.) | 1.91 | 5.19 | | | | 2.95 | 3.41 |
| s | .18 | .74 | | | | .24 | .10 |
| Victa (Marysville, O.) | 1.38 | 4.96 | 45.45 | 4.20 | 5.84 | 2.68 | 2.90 |
| s | .20 | .60 | 3.22 | .63 | 1.69 | .12 | .14 |
| Victa (Salem, Ore.) | 1.81 | 4.82 | 64.69 | 4.90 | 15.72 | 2.41 | 2.79 |
| s | .16 | .61 | 6.94 | .57 | 2.35 | .30 | .22 |
| Merion (Marysville, O.) | 1.32 | 4.58 | 48.46 | 3.70 | 8.55 | 2.04 | 2.38 |
| s | .19 | .78 | 2.78 | .82 | 2.23 | .31 | .19 |
| Newport (Marysville, O.) | 1.53 | 3.81 | 54.88 | 3.10 | 13.35 | 2.83 | 3.12 |
| s | .22 | .69 | 2.88 | .32 | 3.86 | .21 | .25 |

[1] s=sample standard deviation.
[2] Flag leaf, one inch from collar.

Mowed plots have been evaluated under turf conditions at Rutgers University, New Brunswick, N.J. and at Accokeek, Md. and Marysville, Ohio. Turfgrass performance information presented indicates the distinctiveness of P–72 compared to other bluegrass varieties and its desirable characteristics and persistence.

Leaf spot (*Helminthosporium* spp.) diseases cause severe plant damage and thinning of bluegrass turf in most locations in the Northern United States and Canada during the months of April, May and June of each year. Table 2 provides leaf spot information in the spring on two-year-old turf grown at Marysville, Ohio. The varieties Merion and Fylking are recognized as having an acceptable and a good level of resistance to leaf spot diseases. In this study P–72 was equal to or better than Merion and Fylking in resistance to leaf spot and significantly stronger in resistance than Park and Kenblue varieties which are considered to be leaf spot susceptible.

TABLE 2

Comparison of the susceptibility of P–72 and other bluegrass varieties as two-year-old turf grown at Marysville, Ohio to the causal organism *Helminthosporium* spp.

| | Percent | |
|---|---|---|
| | May | June |
| Variety: | | |
| P–72 | 10 | 18 |
| Merion | 15 | 17 |
| Fylking | 35 | 18 |
| Park | 67 | 60 |
| Kenblue | 72 | 57 |

Rating scale; Number indicates percent of disease incidence in plot.

In a five-year-study at New Brunswick (Table 3) the average percent leaf spot damage caused by *Helminthosporium vagans* was only three percent which again was equal to or better than the accepted resistant varieties of Merion and Fylking. It was significantly more resistant than Delta which has been established as a highly susceptible variety. In this study P–72 leaf spot resistance was equal to Anheuser Dwarf, the male parent, and significantly more resistant than its female parent Bellevue.

TABLE 3

Comparison of P–72 and other bluegrass varieties on five-year-old turf at Rutgers University to the resistance of *Helminthosporium vagans*

| Variety: | Percent disease damage |
|---|---|
| P–72 | 3 |
| Bellevue (female parent) | 10 |
| Anheuser Dwarf (male parent) | 2 |
| Fylking | 6 |
| Merion | 5 |
| Delta | 70 |

Rating scale: Number indicates percent disease damage in plot.

Four-year-old turf of P–72 also provided a strong level of leaf spot resistance (Table 4) at Rutgers University rated in two different leaf spot months—April and June. Again in this study it was significantly more resistant than the common types such as Kenblue, Park and Geary.

TABLE 4

Comparison of P–72 and other bluegrass varieties on four-year-old turf in two different months at Rutgers University to the resistance of *Helminthosporium* spp.

| | Percent disease | |
|---|---|---|
| | April 10 | June 5 |
| Variety: | | |
| P–72 | 5 | 4 |
| Fylking | 8 | 7 |
| Kenblue | 85 | 91 |
| Park | 65 | 95 |
| Geary | 52 | 86 |

Rating scale: Number indicates percent disease in plot.

Stripe smut (*Ustilago striiformis*) will affect susceptible varieties to the point of thinning the turf and in extreme cases will completely kill large areas of turf. Stripe smut is generally most severe on turf that is at least two years of age or older. Bluegrass varieties that were four years of age were evaluated as to stripe smut resistance by counting the number of infected tillers per square foot. Table 5 indicates that P–72 has only eight infected tillers per square foot compared to Fylking and Pennstar which had 20 and 14 infected tillers respectively and they are considered to have a good level of stripe smut resistance. Susceptible varieties Merion and Newport had 433 and 193 infected tillers respectively.

TABLE 5

Comparison of P–72 and other bluegrass varieties on four-year-old turf at Rutgers University as to number of stripe smut infected tillers per square foot

| Variety: | Number of infected tillers |
|---|---|
| P–72 | 8 |
| Fylking | 20 |
| Pennstar | 14 |
| Merion | 433 |
| Newport | 193 |

Rating scale: Number indicates number of stripe smut infected tillers per square foot.

Fusarium blight or *Fusarium roseum* is quite prevalent in the transition grass zone areas during the hot dry periods of the year normally occurring in July and August. When a *Fusarium* epidemic occurs complete lawns may be destroyed with limited regrowth except for weeds. Severe infestations of *Fusarium roseum* have been observed in the Washington, D.C. area over the past few years. Most bluegrass varieties are quite susceptible; however, P–72 Kentucky bluegrass has shown a good level of resistance. Table 6 indicates P–72 level of resistance as a young two-year-old turf compared to Loba which is quite susceptible and to Ba 61–24, Plant Pat. 3,032, which has a high level of *Fusarium roseum* resistance as shown in Table 7, the same plots at the end of four years continue to indicate the good level of resistance P–72 has throughout the summer months compared to the susceptible variety Loba. However some light *Fusarium roseum* activity was noted in four-year-old turf which indicates the level of resistance as slightly less than Ba 61–24.

TABLE 6

Comparison of P–72 and other bluegrass variety on two-year-old turf at Accokeek, Maryland as to the resistance of *Fusarium roseum*

| | Percent *Fusarium* damage | | |
|---|---|---|---|
| | August | September | October |
| Variety: | | | |
| P–72 | 0 | 0 | 0 |
| Windsor | 2 | 12 | 18 |
| Common Kentucky | 5 | 10 | 15 |
| Primo | 8 | 25 | 30 |
| Loba | 10 | 40 | 45 |
| Ba 61–24 (Vantage) | 0 | 1 | 0 |

Rating scale: Number indicates percent *Fusarium roseum* damage in plot.

TABLE 7

Comparison of P–72 and other bluegrass varieties on four-year-old turf at Accokeek, Md. as to the resistance of *Fusarium roseum*

| | Percent *Fusarium roseum* damage | | |
|---|---|---|---|
| | July | August | September |
| Variety: | | | |
| P–72 | 0 | 25 | 15 |
| Windsor | 2 | 35 | 23 |
| Common Kentucky | 10 | 25 | 25 |
| Primo | 22 | 45 | 32 |
| Loba | 10 | 65 | 55 |
| Ba 61–24 (Vantage) | 0 | 5 | 5 |

Rating scale: Number indicates percent *Fusarium roseum* damage in plot.

Turf quality, a rating taking all turfgrass performance characteristics together and assigning it a value, was measured at Rutgers University and at Accokeek, Md. and Marysville, Ohio. A rating scale of 1 to 9 with 9 having best turf quality was used at Rutgers University. The average placed P–72 in the upper ten percent of the fifty bluegrass varieties evaluated in the 1968 regional Kentucky bluegrass trials. P–72 turf quality was rated above all of the common types and many of the improved types (Table 8).

TABLE 8

Comparison of P–72 and other bluegrass varieties on four-year-old turf at Rutgers University as to turf quality over an entire growing season

| Variety | Turf quality rating |
|---|---|
| P–72 | 6.5 |
| Fylking | 6.9 |
| Sodco | 6.5 |
| Kenblue | 3.0 |
| Park | 2.9 |

Rating Scale: 1=poor; 9=best.

The Accokeek, Md. and Marysville, Ohio locations used a 1 to 4 rating scale for turf quality with 4 being the best turf. Again P–72 was equal to or better than the improved varieties and was rated better than the common types throughout the growing season (Tables 9 and 10).

TABLE 9

Comparison of P–72 and other bluegrass varieties on three-year-old turf at Accokeek, Md. as to turf quality

| | Turf quality rating | | | | |
|---|---|---|---|---|---|
| | April | June | July | Sept. | Oct. |
| Variety: | | | | | |
| P–72 | 2 | 2.5 | 2.5 | 3 | 3.5 |
| Windsor | 1.7 | 1.7 | 2 | 1.8 | 2.7 |
| Common Kentucky | 2 | 1 | 1 | 2 | 2 |
| Primo | 1 | 1.5 | 1 | 1.2 | 2 |
| Loba | 1 | 1.5 | 1 | 1 | 1 |

Rating scale: 1=poor turf; 4=best turf.

TABLE 10

Comparison of P–72 and other bluegrass varieties on two-year-old turf at Marysville, Ohio as to turf quality

| | Turf quality rating | | | | |
|---|---|---|---|---|---|
| | April | May | June | July | August |
| Variety: | | | | | |
| P–72 | 2.5 | 4 | 2.8 | 2.5 | 2.3 |
| Merion | 2 | 2.2 | 2.8 | 3.3 | 2.2 |
| Fylking | 2 | 2 | 2 | 2.2 | 2 |
| Park | 1.7 | 1 | 1.3 | 1.2 | 1.5 |
| Kenblue | 1 | 1.3 | 1.2 | 1.2 | 1.7 |

Rating scale: 1=poor turf; 4=best turf.

Powdery mildew which is a fungus and produces a gray white cobwebby growth on the upper surface of the leaves is normally found on bluegrass plants grown under restricted levels of light such as found under trees. This disease blocks out sunlight and therefore reduces photosynthetic rate. If this condition persists for any length of time the grass plant will become weak and may eventually die. P–72 was found to possess a good level of powdery mildew resistance both at Rutgers University in a greenhouse study and at Marysville, Ohio in natural shaded areas (Tables 11 and 12).

TABLE 11

Comparison of P–72 and other bluegrass varieties at

Rutgers University as to powdery mildew resistance in the greenhouse

| Variety | Powdery mildew incidence |
|---|---|
| P–72 | 0.9 |
| Merion | 6.5 |
| Pennstar | 4.2 |
| A–34 | 1.8 |

Rating scale: 1=least amount of powdery mildew; 9=most amount of powdery mildew.

TABLE 12

Comparison of P–72 and other bluegrass varieties at Marysville, Ohio as to powdery mildew resistance in natural tree shade

| | Powdery mildew incidence | |
|---|---|---|
| | October | November |
| Variety: | | |
| P–72 | 0 | 7 |
| Merion | 92 | 93 |
| Pennstar | 75 | 80 |

Rating scale: Number indicates percent powdery mildew incidence in plot.

Seed counts and measurements indicate that P–72 Kentucky bluegrass produces large seed when grown in the Pacific Northwest. Seed number per pound is slightly below one million (944,660) compared to a few other commercial varieties with seed counts ranging from 1.2 to over 2 million seeds per pound (Table 13).

TABLE 13

Comparison of P–72 and other Kentucky bluegrass varieties as to the number of seeds produced per pound in the Pacific Northwest

| | Number of seeds per pound | Standard deviation |
|---|---|---|
| Variety: | | |
| P–72 | 944,660 | 20.40 |
| Merion | 1,710,105 | 44.01 |
| Kenblue | 2,239,885 | 102.25 |
| Park | 1,405,432 | 15.01 |
| Newport | 1,258,034 | 25.77 |

Note: Number of seeds per pound were determined by counting one gram lots using an electric seed counter.

Chromosome counts were made of P–72 bluegrass at Rutgers University and Scotts laboratories, Marysville, Ohio. The approximate chromosome number of P–72 was estimated as 95. In a study at Scotts, 75 chromosome examinations were made. From this study the somatic chromosome number of P–72 was estimated as 98 or a range of 97±3. The chromosome number of the seed parent Bellevue was reported as 2n=56 and the pollen parent Anheuser Dwarf 2n=72. These chromosome counts indicate that this is a triploid from fertilization of unreduced eggs by reduced male gametes or vice versa, 3n=92 or 100.

What is claimed and desired to be secured by Letters Patent is:

1. A variety of bluegrass plant, substantially as shown and described.

References Cited

Intraspecific Hybridization . . ., Pepin et al., Crop Science, vol. II, May-June 1971, pp. 445–8, relied on.

ROBERT E. BAGWILL, Primary Examiner